United States Patent
Guay et al.

[11] Patent Number: 6,018,840
[45] Date of Patent: Feb. 1, 2000

[54] NOTCHED DENTAL HYGIENE ARTICLE

[75] Inventors: Gordon G. Guay, Chelmsford; Ronald R. Duff, Jr., Shrewsbury, both of Mass.

[73] Assignee: Gillette Canada Inc., Kirkland, Canada

[21] Appl. No.: 09/037,115

[22] Filed: Mar. 9, 1998

[51] Int. Cl.[7] .................................................. A46B 9/04
[52] U.S. Cl. ........................................ 15/207.2; 15/167.1
[58] Field of Search .............................. 15/167.1, 207.2; 428/400, 399, 398

[56] References Cited

U.S. PATENT DOCUMENTS

| | | | |
|---|---|---|---|
| 2,317,485 | 4/1943 | Rider | 15/167.1 |
| 2,637,893 | 5/1953 | Shaw | 15/207.2 |
| 2,790,986 | 5/1957 | Schwartz et al. | 15/192 |
| 2,876,477 | 3/1959 | Stewart | 15/167.1 |
| 3,118,527 | 1/1964 | Lombardy et al. | 192/107 M |
| 3,295,156 | 1/1967 | Brant | 15/167.1 |
| 3,325,845 | 6/1967 | Sawkiw | 15/207.2 |
| 3,344,457 | 10/1967 | Grobert | 15/207.2 |
| 3,411,979 | 11/1968 | Lewis, Jr. | 428/398 |
| 3,425,206 | 2/1969 | Holton | 57/208 |
| 3,505,163 | 4/1970 | Meers et al. | 428/371 |
| 3,567,569 | 3/1971 | Ono et al. | 428/399 |
| 4,186,239 | 1/1980 | Mize et al. | 428/400 |
| 4,373,541 | 2/1983 | Nishioka | 15/167.1 |
| 4,524,480 | 6/1985 | Bloom | 15/207.2 |
| 4,616,374 | 10/1986 | Novogrodsky | 15/167.1 |
| 5,161,555 | 11/1992 | Cansler et al. | 132/218 |
| 5,195,546 | 3/1993 | Cansler et al. | 132/317 |
| 5,268,005 | 12/1993 | Suhonen | 8/504 |
| 5,467,495 | 11/1995 | Boland et al. | 15/28 |
| 5,491,865 | 2/1996 | Gueret | 15/159.1 |
| 5,678,275 | 10/1997 | Derfner | 15/207.2 |
| 5,701,629 | 12/1997 | O'Brien | 15/207.2 |

FOREIGN PATENT DOCUMENTS

| | | |
|---|---|---|
| 2757046 | 7/1979 | Germany. |
| 3116-189 | 12/1982 | Germany. |
| 41 14 136 A1 | 4/1991 | Germany. |
| 94 08 268 U | 8/1994 | Germany. |
| 295 01 338 | 1/1995 | Germany. |
| 295 01 338 U1 | 8/1995 | Germany. |
| 195 19 026 | 8/1996 | Germany. |
| 196 15 098 A1 | 10/1997 | Germany. |
| 141929 | 5/1994 | Japan ........... 15/207.2 |
| 15641 | 12/1897 | Switzerland. |
| 598821 | 2/1948 | United Kingdom. |

OTHER PUBLICATIONS

United States Patent Application Serial No. 08/886,425.
Walczak, "Formation of Synthetic Fibers", *Practical Applications*, pp. 310–311 and 318 (1977).
Ullmann's Encyclopedia of Industrial Chemistry, vol. A 11, Fibers, 5. Synthetic Inorganic to Formaldehyde, pp. 75–76.
United States Application Serial No. 08/675,096.
United States Application Serial No. 08/879,730.
International Organization for Standardization, International Standard ISO 8627:1987(E), Ondontology.

*Primary Examiner*—Robert J. Warden, Sr.
*Assistant Examiner*—Theresa T. Snider
*Attorney, Agent, or Firm*—Fish & Richardson P.C.

[57] ABSTRACT

A dental hygiene article including a notched filament. The dental hygiene article can be a dental floss, or an oral brush (e.g., an electronic toothbrush, a manual toothbrush, or an interdental brush).

45 Claims, 7 Drawing Sheets

NOTCHED DENTAL HYGIENE ARTICLE

BACKGROUND OF THE INVENTION

This invention relates to dental hygiene articles.

Most people suffer from tooth decay and/or gingivitis caused by plaque in the mouth. As a result, reducing the amount of plaque in the mouth has long been the target of persons working in the health care field. Regularly brushing the teeth using toothbrushes and flossing between teeth using dental floss are common ways of minimizing plaque build up in the mouth.

Toothbrushes generally include a toothbrush body that includes a handle portion and a head portion. The head portion includes tufts of bristles.

Dental floss generally includes a fiber core made up of one or more continuous filaments.

SUMMARY OF THE INVENTION

The invention features dental hygiene articles (e.g., toothbrushes and dental floss) that include notched bristles or fibers. These notched bristles are preferably formed by cutting notched elongated filaments to a suitable length for use as bristles. Notched elongated filaments can also be used as the fiber core of a dental floss. By "notched", it is meant that the filament has a plurality of cuts (e.g., v-shaped cuts or slits). The cuts can exist in a variety of configurations on the filament, e.g., in regularly spaced intervals (i.e., the notches are in the form of regularly repeating cuts, e.g., cuts aligned in a pattern, cuts aligned linearly along the length of the filament (e.g., serrated), cuts aligned around the circumference of the filament, and combinations thereof); in irregularly spaced intervals (i.e., randomly occurring cuts); and in various permutations thereof.

The term "notches", as used herein, is intended to include both the cut and the protrusion(s) that extend from the filament as a result of the cut (e.g., the lip formed at the entrance to the cut, and the serrated protrusions that extend from the filament surface when the notches define a serrated pattern).

In one aspect, the dental hygiene article is an oral brush that includes a body and bristles that include notches extending from the body.

In another aspect, the invention features a dental hygiene article that includes a body and a notched bristle extending from the body.

The notches may occur at regular intervals, irregular intervals, and in combinations thereof. The notches may also define a serrated pattern. In one embodiment, the notches extend into a bristle at substantially the same angle to the bristle surface. In another embodiment, one of the notches extends into a bristle at a first angle to the bristle surface and a second of the notches extends into the bristle at a second angle to the bristle surface. The first angle is different from the second angle.

Preferably the bristles include a cylindrical core and at least one protrusion extending from the cylindrical core. Notches are located on the protrusion(s). In preferred embodiments, the bristle includes two, three, or four protrusions defining a variety of shapes including, e.g., a star shape, a Y-shape and an X-shape. The bristles may be arranged in a tuft extending from the body.

In another aspect, the invention features a notched bristle for an oral brush.

In other aspects, the invention features a method of using the above-described dental hygiene articles. The method includes contacting the teeth of a mammal with notched bristles. The method can further include the step of applying a dentifrice to the bristles prior to contacting the teeth with the bristles.

In another aspect, the invention features a method of making a toothbrush that includes affixing notched bristles to a toothbrush body. In one embodiment, the method further includes cutting notches into a filament and forming the filament into notched bristles. The step of cutting includes passing a filament between at least two opposed cutting edges.

In other aspects, the invention features a dental floss that includes a fiber core having notches. Preferably the fiber core includes filaments. In another aspect, the invention features a method of flossing the teeth of a mammal that includes inserting the above-described dental floss between two teeth of the mammal.

The notched bristles aid in cleaning the oral surface by allowing a roughened surface to contact the oral surface. The notches create resistance (e.g., by gripping) against the oral surface, which aids in cleaning the oral surface.

Other features and advantages will be apparent from the following description of the preferred embodiments thereof, and from the claims.

BRIEF DESCRIPTION OF THE DRAWINGS

FIG. 19b is an enlarged perspective view of the brush head of FIG. 19a.

DESCRIPTION OF THE PREFERRED EMBODIMENTS

Figure 1:
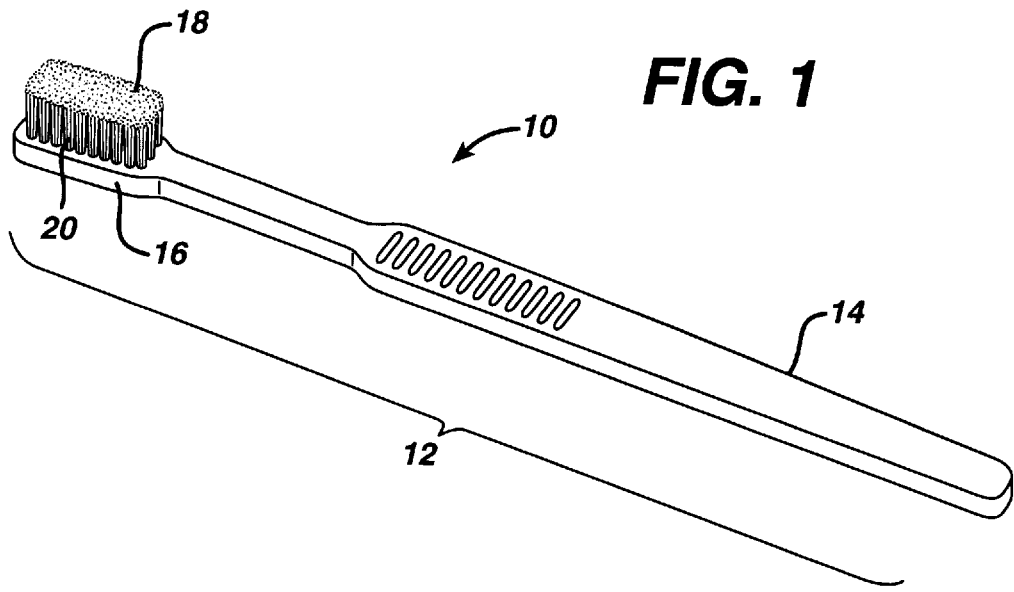
FIG. 1 is a perspective view of an oral brush according to one embodiment of the invention.

Referring to FIG. 1, toothbrush 10 includes a body 12 having a handle 14 and a head 16, and a bristle portion 18 attached to the head 16.

Body 12 of toothbrush 10 is formed by conventional methods well-known in the art. The handle is shaped to be grasped by a hand, but alternatively can be shaped to fit into an electric toothbrush. The configuration of the head can vary and may be rectangular, oval, diamond shaped, or any other shape. The unsecured ends of the bristles can be trimmed flat, v-shaped, serrated, convex curved, or any other desired topography. The shape and size of handle 14 and head 16 can vary and the axis of the handle and head may be on the same or a different plane. Bristle portion 18 is formed of one or more tufts of individual bristles attached to the head in manners known to the art, e.g., stapling or hot-tufting.

Figure 2:
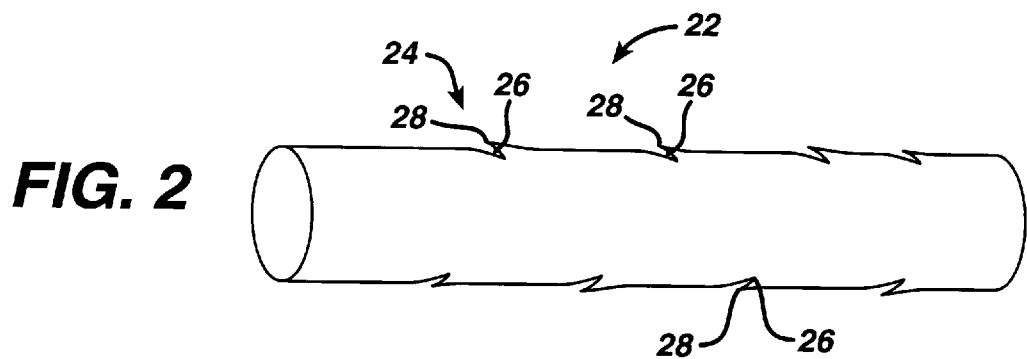
FIG. 2 is a highly enlarged side view of a notched filament.
Figure 3:
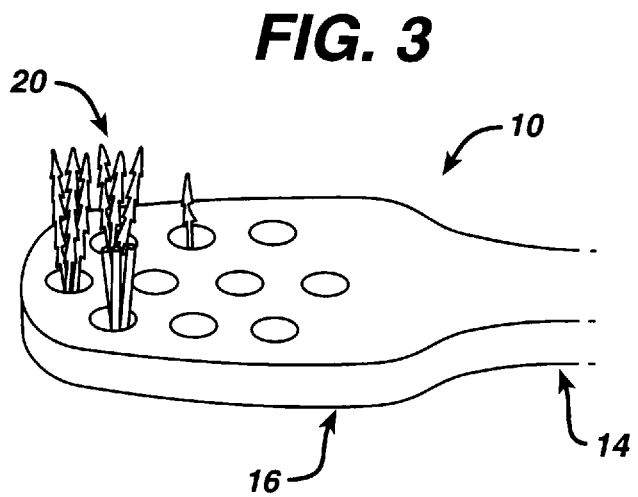
FIG. 3 is a highly enlarged perspective view of the head of the oral brush of FIG. 1.

Notched filament 22 including cuts 26 and protrusions 28 is shown in FIG. 2. Notched filaments are cut to form the notched bristles 20 of bristle portion 18 of toothbrush 10. Any materials suitable for use in oral brush bristles can be used to form the notched bristles, provided that a notch can be imparted to the material. Preferred bristle materials are capable of being notched and when notched have the stiffness characteristics and structural integrity of conventional cylindrical bristles. Preferably the notched bristles have a stiffness grade (ISO 8627) of from about 2 to 7 cN/mm$^2$.

Examples of suitable bristle materials include, but are not limited to, Nylon 612, PBT, PVDF, acetal resins, polyesters, fluoropolymers, polyacrylates, polysulfones, and mixtures thereof. Bristles may contain PTFE (polytetrafloroethylene), kaolin, or other fillers or additives. The bristles can each include a blend of polymers, or bristles of different polymers may be mounted on the same oral brush. If the bristles include a blend of polymers, the polymers can either be blended to form a single phase, or maintained in separate phases and co-extruded together in any desired configuration, e.g., with one polymer forming a sheath surrounding another polymer (sheath/core) or polymers in a side-by-side configuration. The bristles can also include a multi-core fiber, individual fibers surrounded by a sheath, and combinations thereof.

Figure 9A:
Figure 9B:
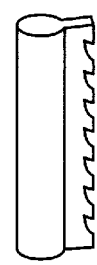
Figure 10:
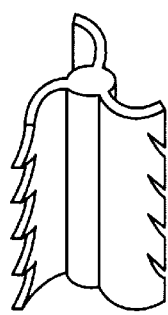
Figure 11:
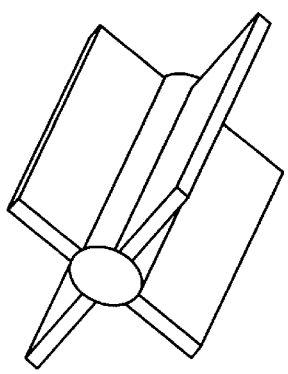
Figure 12:
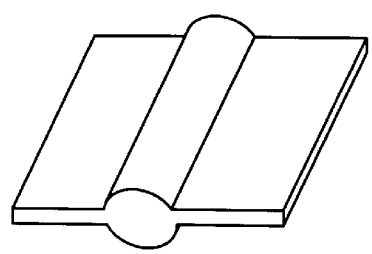
Figure 13:
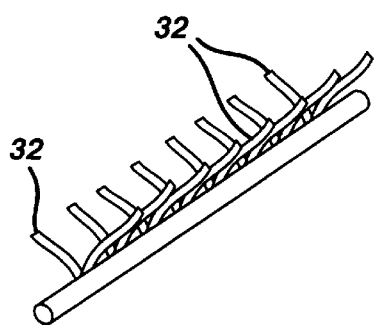
Figure 14:
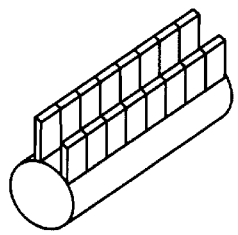

The bristles can have a substantially uniform cross-sectional dimension of between about 0.003 in. to about 0.1 in. The bristles can be in the shape of a cylinder having notches as shown in FIGS. 4–7. Bristles having a variety of shapes and configurations are also suitable. For example, the notched bristles can include a central cylindrical core and at least one protrusion extending from the cylindrical core as shown in FIGS. 8–14 and 23–25. The protrusion(s) can be notched. Examples of such bristles include keyhole shaped bristles as shown in FIGS. 9a and 9b, X-shaped bristles as shown in FIG. 11, Y-shaped bristles as shown in FIG. 10, and U-shaped bristles as shown in FIG. 14. A bristle having a single protrusion extending from a cylindrical core and a series of notches cut into the protrusion in the form a serrated pattern is shown in FIG. 8. Referring to FIG. 13, sections 32 of the bristle material defined by the notches can be bent or altered such that some of the individual sections are not in alignment with each other.

Figure 5:
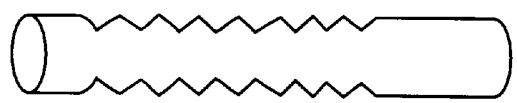
FIG. 5 is an enlarged perspective view of a notched bristle according to a third embodiment of the filament of FIG. 2.
Figure 6:
FIG. 6 is an enlarged perspective view of a notched bristle according to a fourth embodiment of the filament of FIG. 2.
Figure 7:
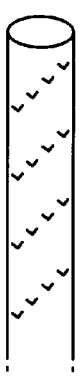
FIG. 7 is an enlarged perspective view of a notched bristle according to a fifth embodiment of the filament of FIG. 2.
Figure 8:
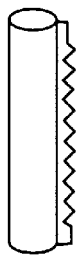
FIGS. 8–14 are enlarged perspective views of notched bristles having a central cylindrical core and one or more protrusions extending from the cylindrical core according to other embodiments of the filament of FIG. 2.

The notches can exist in a variety of configurations on the filament including, e.g., regularly spaced intervals (e.g., a pattern of notches circling the circumference of the bristle as shown in FIGS. 6 and 7, and a serrated pattern of notches extending linearly between the ends of the bristle as shown in FIGS. 5 and 8), irregularly spaced intervals (e.g., notches occurring randomly about the bristle), and combinations thereof.

The notches can extend into the bristle to any desired depth. It is preferred, however, that the bristle maintain its structural integrity such that it can perform the brushing function without rapid deterioration of performance.

Figure 4:
FIG. 4 is an enlarged perspective view of a notched bristle according to a second embodiment of the filament of FIG. 2

The angle defined by the cut of the notch and the bristle surface can be the same for each notch, can vary from notch to notch, or can exist in various permutations thereof as shown in FIG. 4. Preferably each of the notches is of the same angle relative to the surface of the bristle.

Each of the notched bristles on a single toothbrush can have substantially the same notched geometry, e.g., each bristle has substantially the same depth of cut for each notch, each notch is cut at substantially the same angle, and notches occur at substantially the same intervals. The toothbrush can also include notched bristles having a variety of notched bristle geometries.

Figure 20:
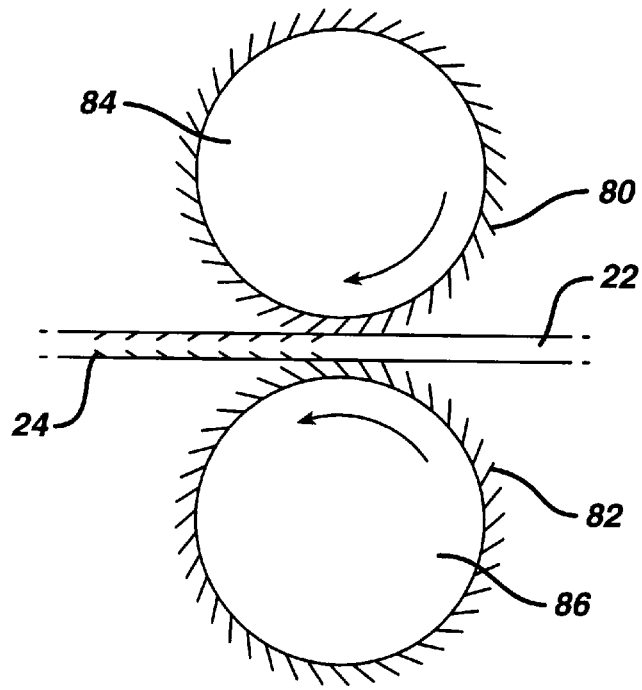
FIG. 20 is a diagrammatic view of a method of imparting notches to a filament according to one embodiment of the invention.
Figure 21:
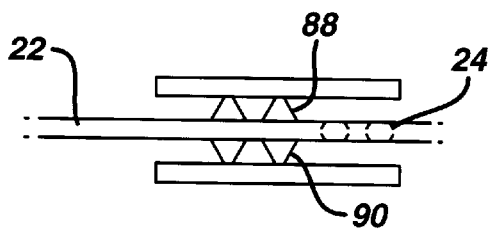
FIG. 21 is a diagrammatic view of a method of imparting notches to a filament according to a second embodiment of the invention.

Suitable methods of imparting notches include mechanical, thermal and chemical methods. One method of imparting notches 24 to filaments 22 includes cutting filament 22 at an angle to the filament surface with a sharp edge, e.g., a knife or blade, as shown in FIGS. 20 and 21. Referring to FIG. 20, filament 22 is passed between a series of opposing blades 80, 82, which impart notches 24 to the filament. The rotation of the blade carriers 84, 86 moves filament 22 so that additional filament is available for notching. Referring to FIG. 21, opposing blades 88, 99 clamp down onto filament 22 to impart notches 24 to filament 22. The space between the two cutting devices can be altered to adjust the depth of notching obtained. The blades can be spaced at the regular intervals or irregular intervals. The angle of the blades can also be adjusted to adjust the angle or angles at which each blade contacts and enters the filament.

The toothbrush may include other types of bristles in combination with the notched bristles, e.g., single and multicomponent bristles (e.g., bristles formed by coextruding different polymers), crimped bristles, gum massaging bristles, bristles of varying configurations, e.g., bristles having multiple lumens, and bristles defining a variety of shapes (e.g., lobular, annular, or polygonal, e.g., square, rectangular, hexagonal, or diamond), conventional cylindrical and combinations thereof.

Figure 15:
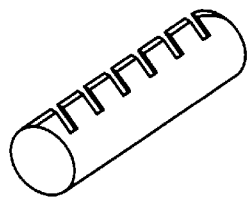
FIG. 15 is an enlarged perspective view of a notched bristle according to a sixth embodiment of the filament of FIG. 2.

The notched bristles can be located in some or all of the perimeter tufts to provide softness against the gums, or can be located in some or all of the interior tufts to provide fullness. Moreover, although a v-shaped notch has been described above, the bristles can have other types of notches including, e.g., slits (as shown in FIGS. 13 and 14), square shaped notches (as shown in FIG. 15), and hemispherical notches.

Figure 17:
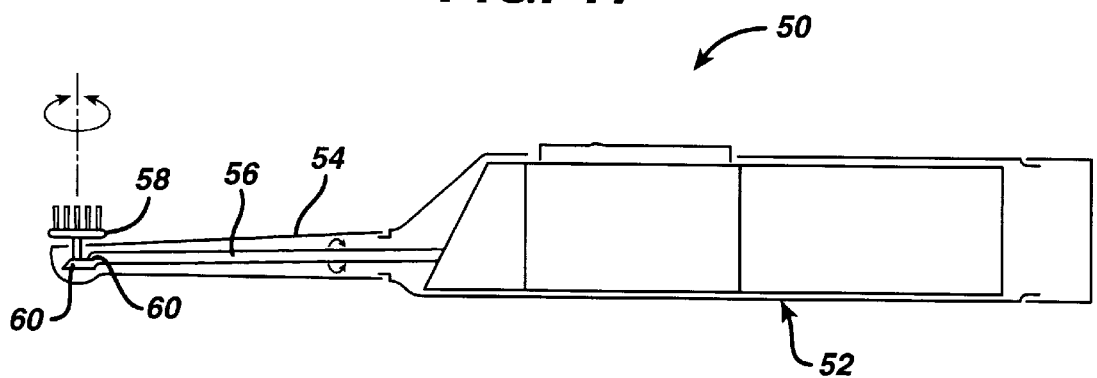
FIG. 17 is a schematic side view of an electric toothbrush according to a third embodiment of the invention.

The oral brush need not be a manual toothbrush having a conventional shape, as shown in FIG. 1, but may be any type of brush designed for brushing teeth that includes a body with bristles extending therefrom. For example, the toothbrush may be any type of electric toothbrush, e.g., a toothbrush 50 having a body 52, a neck 54, a drive shaft 56, and a head 58 operably connected to the drive shaft 56, by a drive mechanism 60 (e.g., a pinion gear), as shown in FIG. 17. Head 58 includes a plurality of notched bristles, and may also, optionally, include a plurality of non-notched bristles.

Figure 18:
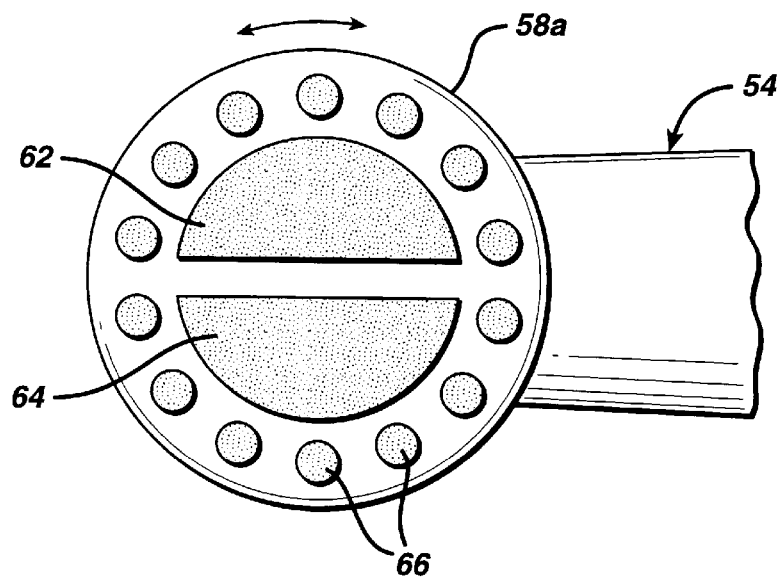
FIG. 18 is an enlarged top view of a first embodiment of the brush head of the toothbrush of FIG. 17.
Figure 19A:
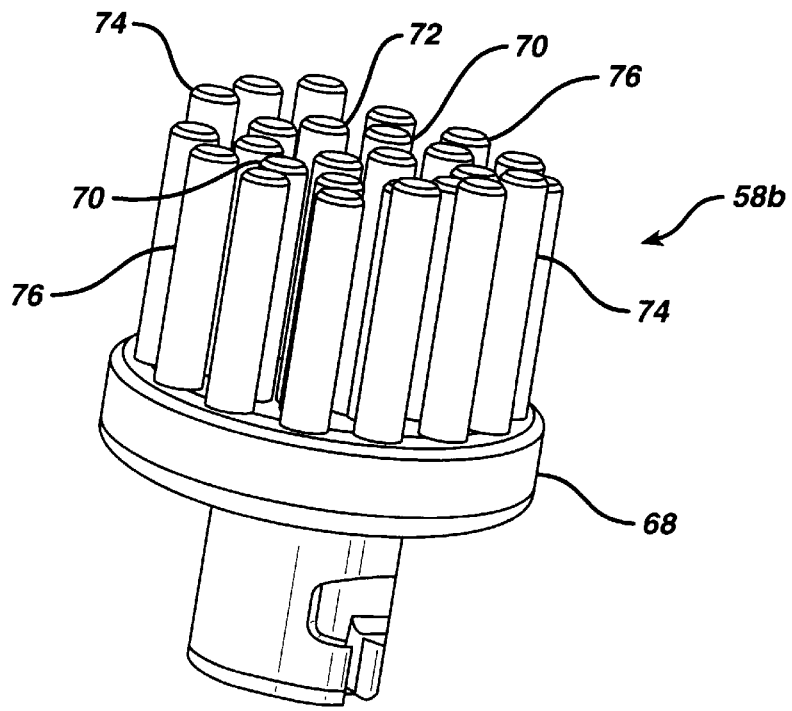
FIG. 19a is an enlarged top view of a second embodiment of the brush head of the toothbrush of FIG. 17.
Figure 19B:
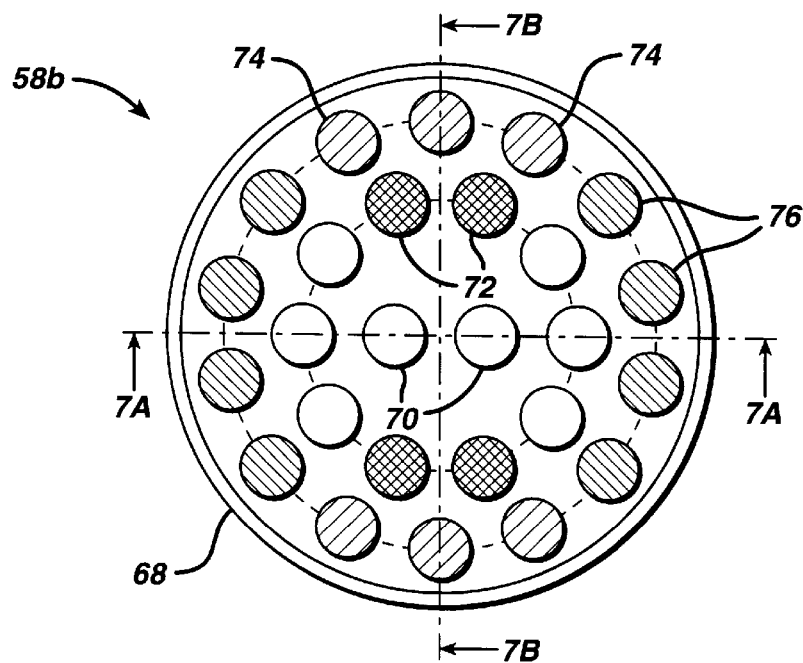

Examples of electric toothbrush heads 58a and 58b are shown in FIGS. 18, 19a and 19b. Head 58a includes a plurality of tufts of notched bristles defining a pair of substantially semicircular brush portions 62 and 64, and further includes a plurality of tufts of non-notched bristles 66 disposed about the periphery of the head.

As shown in greater detail in FIGS. 19a and 19b, head 58b has an array of tufts 70 of notched bristles extending from a body 68 and arranged with tufts 72 and 74 of cylindrical bristles dyed with a wear indicator, and tufts 76 of undyed cylindrical bristles. The different types of tufts are shown with different cross hatching for illustration in FIG. 19b. Notched tufts 70 and cylindrical dyed tufts 72 make up the inner field of tufts, while cylindrical dyed tufts 74 and cylindrical undyed tufts 76 make up the outer row of tufts.

Figure 16:
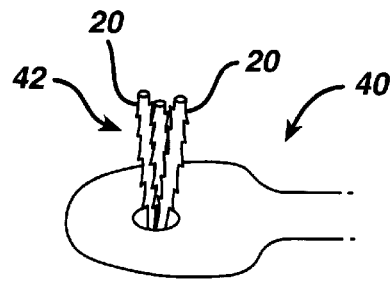
FIG. 16 is a highly enlarged perspective view of a head of an oral brush according to a second embodiment of the invention.
Figure 22:
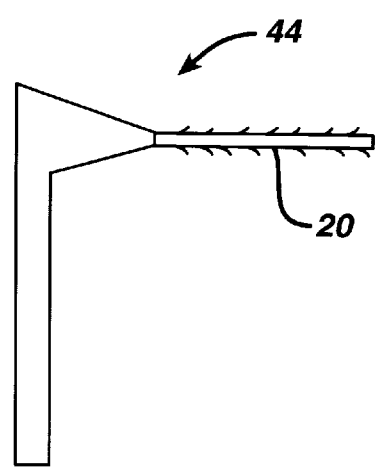
FIG. 22 is a side view of an oral brush according to a third embodiment of the invention.
Figure 23:
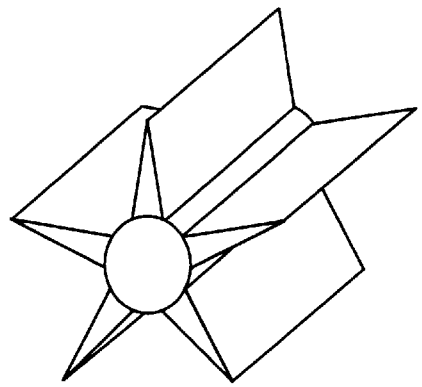
FIGS. 23–25 are enlarged perspective views of notched bristles having a cylindrical core and one or more protrusions extending from the cylindrical core according to other embodiments of the filament of FIG. 2.
Figure 24:
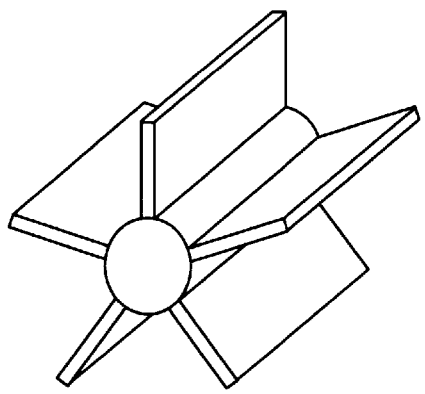
Figure 25:
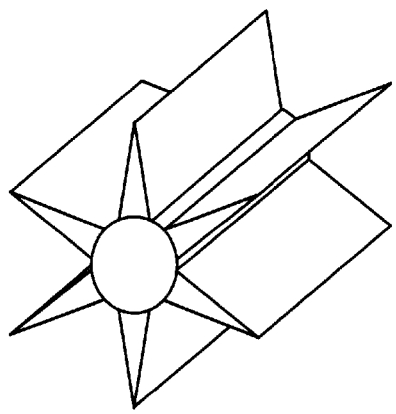

Other embodiments are within the claims. For example, the dental hygiene article can be in the form of an oral brush 40, 44 for brushing the interdental regions of the mouth as shown in FIGS. 16 and 22. Such an oral brush can include a single notched bristle 20 or a number of notched bristles 20 arranged in a single tuft 42.

In another aspect, the dental hygiene article is in the form of a dental floss including a filament having notches. The dental floss can include a single notched filament or a plurality of notched filaments, e.g., a plurality of filaments intertwined or braided to form a dental floss. Materials suitable for dental floss filaments include the materials listed above with respect to bristle filaments and nylon 6. Such materials are preferably sufficiently strong to resist shearing or breakage under standard floss testing conditions.

What is claimed is:

1. An oral brush comprising:
   a body; and
   bristles extending from said body,
   said bristles comprising notches at regular intervals along said bristles, each notch being defined by
   1) a slit extending into said bristle from an exterior surface of said bristle, and
   2) a protrusion overlapping said slit.

2. The oral brush of claim 1, wherein said slits extend into said bristle at substantially the same angle to the bristle surface.

3. The oral brush of claim 1, wherein one of said slits extends into said bristle at a first angle to the bristle surface and a second of said slits extends into said bristle at a second angle to the bristle surface, said first angle being different from said second angle.

4. The oral brush of claim 1 wherein said bristles comprise a cylindrical core and at least one protrusion extending from said cylindrical core, said notches being located on said protrusion.

5. The oral brush of claim 4 wherein said bristles define a star shape.

6. The oral brush of claim 1 wherein said bristles comprise a cylindrical core and two protrusions extending from said cylindrical core, said notches being located on said protrusions.

7. The oral brush of claim 1 wherein said bristles comprise a cylindrical core and three protrusions extending from said cylindrical core, said notches being located on said protrusions.

8. The oral brush of claim 7 wherein said bristles define a Y-shape.

9. The oral brush of claim 1 wherein said bristles comprise a cylindrical core and four protrusions extending from said cylindrical core, said notches being located on said protrusions.

10. The oral brush of claim 9 wherein said bristles define an X-shape.

11. The oral brush of claim 1 wherein said notched bristles are arranged in a tuft extending from said body.

12. The oral brush of claim 1, further comprising bristles that are free of notches.

13. The oral brush of claim 1, wherein a first plurality of said bristles comprise notches defined by slits extending toward a free end of said bristle; and
   a second plurality of said bristles comprise notches defined by slits extending toward a secured end of said bristle.

14. The oral brush of claim 1, wherein said bristles comprise a first free end and a second end secured to said body, and said slits of said notches extend toward said first end of said bristles.

15. The oral brush of claim 1, wherein said bristles comprise a first free end and a second end secured to said body, and slits of said notches extend toward said second end of said bristles.

16. A bristle for an oral brush comprising:
   a bristle comprising notches at regular intervals along said bristle, each notch being defined by
   1) a slit extending into said bristle from an exterior surface of said bristle, and
   2) a protrusion overlapping said slit.

17. An oral brush comprising:
   a body; and
   a bristle comprising notches extending from said body, each-notch being defined by
   1) a slit extending into said bristle from an exterior surface of said bristle, and
   2) a protrusion overlapping said slit.

18. An oral brush comprising:
   a body; and
   bristles extending from said body,
   said bristles comprising notches, a cylindrical core, and at least one protrusion extending from said cylindrical core,
   said notches being located on said protrusion.

19. The oral brush of claim 18, wherein said bristles define a star shape.

20. The oral brush of claim 18, wherein said bristles comprise two protrusions extending from said cylindrical core, said notches being located on said two protrusions.

21. The oral brush of claim 18, wherein said bristles comprise three protrusions extending from said cylindrical core, said notches being located on said three protrusions.

22. The oral brush of claim 21, wherein said bristles define a Y-shape.

23. The oral brush of claim 18, wherein said bristles comprise four protrusions extending from said cylindrical core, said notches being located on said four protrusions.

24. The oral brush of claim 23, wherein said bristles define an X-shape.

25. The oral brush of claim 18, wherein said bristles are arranged in a tuft extending from said body.

26. The oral brush of claim 18, wherein said notches occur at regular intervals.

27. The oral brush of claim 18, wherein said notches occur at irregular intervals.

28. The oral brush of claim 18, wherein said notches define a serrated pattern.

29. The oral brush of claim 18, wherein said notches comprise slits.

30. The oral brush of claim 18, wherein said notches extend from said bristle at substantially the same angle to the bristle surface.

31. The oral brush of claim 18, wherein one of said notches extends from a bristle at a first angle to the bristle surface, and a second of said notches extends from the bristle at a second angle to the bristle surface, said first angle being different from said second angle.

32. The oral brush of claim 18, wherein said brush is an electric toothbrush.

33. The oral brush of claim 18, further comprising bristles that are free of notches.

34. The oral brush of claim 18, wherein said bristles have a first free end, a second end secured to said body, and an exterior surface, said notches being defined by a slit extending into said bristle from said exterior surface toward one of said first end or said second end of said bristle.

35. The oral brush of claim 34, wherein said slits of said notches extend toward said first end of said bristles.

36. The oral brush of claim 34, wherein said slits of said notches extend toward said second end of said bristles.

37. The oral brush of claim 34, wherein a first plurality of said bristles have notches defined by slits extending toward said first end; and a second plurality of said bristles have notches defined by slits extending toward said second end.

38. An oral brush comprising:

a body; and bristles extending from said body, said bristles comprising notches, each notch being defined by 1) a slit extending into said bristle from an exterior surface of said bristle, and 2) a protrusion overlapping said slit.

39. The oral brush of claim 38 wherein said notches are v-shaped.

40. The brush of claim 38, wherein said bristles comprise a first free end, and a second end secured to said body, said slits extending into said bristle from an exterior surface of said bristle toward said second end of said bristle.

41. The brush of claim 38, wherein said bristles comprise a first free end, and a second end secured to said body, said slits extending into said bristle from an exterior surface of said bristle toward said free end of said bristle.

42. The brush of claim 38, wherein said bristles comprise a first free end and a second end secured to said body, a first plurality of said slits extending into said bristle from an exterior surface of said bristle toward said free end of said bristle, and a second plurality of said slits extend into said bristle from said exterior surface of said bristle toward said second end of said bristle.

43. The brush of claim 38, wherein said notches occur at irregular intervals.

44. The brush of claim 38, wherein said notches define a serrated pattern.

45. A bristle for an oral brush comprising:

a bristle comprising notches, each notch being defined by 1) a slit extending into said bristle from said exterior surface of said bristle, and 2) a protrusion overlapping said slit.

* * * * *